(12) United States Patent
Taniguchi

(10) Patent No.: US 7,452,338 B2
(45) Date of Patent: Nov. 18, 2008

(54) INTRACOELOMIC MOBILE BODY, AND CAPSULE-TYPE ULTRASONIC ENDOSCOPE

(75) Inventor: Yuko Taniguchi, Hachioji (JP)

(73) Assignee: Olympus Corporation, Tokyo (JP)

( * ) Notice: Subject to any disclaimer, the term of this patent is extended or adjusted under 35 U.S.C. 154(b) by 393 days.

(21) Appl. No.: 10/981,054

(22) Filed: Nov. 4, 2004

(65) Prior Publication Data
US 2005/0119577 A1 Jun. 2, 2005

(30) Foreign Application Priority Data
Nov. 6, 2003 (JP) ............................. 2003-377487
Oct. 4, 2004 (JP) ............................. 2004-291679
Oct. 29, 2004 (JP) ............................. 2004-316929

(51) Int. Cl.
*A61B 5/117* (2006.01)

(52) U.S. Cl. ................ 600/593; 600/549; 600/561; 600/437; 600/309; 600/562; 600/101; 600/109; 600/118; 600/160

(58) Field of Classification Search .......... 600/444–446, 600/593, 549, 561, 309, 437, 562, 101, 109, 600/118, 160
See application file for complete search history.

(56) References Cited

U.S. PATENT DOCUMENTS

| | | | |
|---|---|---|---|
| 3,779,234 A * | 12/1973 | Eggleton et al. | 600/466 |
| 3,955,561 A * | 5/1976 | Eggleton | 600/446 |
| 4,282,879 A * | 8/1981 | Kunii et al. | 600/445 |
| 4,330,874 A * | 5/1982 | Sorwick | 367/103 |
| 4,375,818 A * | 3/1983 | Suwaki et al. | 600/463 |
| 4,399,822 A * | 8/1983 | Theumer | 600/445 |
| 4,834,102 A * | 5/1989 | Schwarzchild et al. | 600/463 |
| 4,869,258 A * | 9/1989 | Hetz | 600/446 |
| 5,681,260 A * | 10/1997 | Ueda et al. | 600/114 |
| 5,833,603 A | 11/1998 | Kovacs et al. | |
| 6,315,732 B1 * | 11/2001 | Suorsa et al. | 600/466 |
| 6,626,834 B2 * | 9/2003 | Dunne et al. | 600/444 |
| 6,911,004 B2 * | 6/2005 | Kim et al. | 600/101 |
| 7,083,579 B2 * | 8/2006 | Yokoi et al. | 600/593 |
| 2003/0020810 A1 | 1/2003 | Takizawa et al. | |
| 2003/0023150 A1 | 1/2003 | Yokoi et al. | |

FOREIGN PATENT DOCUMENTS

| | | |
|---|---|---|
| JP | H9-135832 | 5/1997 |
| JP | 2002-306491 | 10/2002 |
| JP | 2003-210395 | 7/2003 |

* cited by examiner

*Primary Examiner*—Brian L. Casler
*Assistant Examiner*—Baisakhi Roy
(74) *Attorney, Agent, or Firm*—Scully, Scott, Murphy & Presser, P.C.

(57) ABSTRACT

An intracoelomic mobile body comprising: a capsule body which has a body to be rotated and can be introduced into the human body; and a rotation drive unit which has a rotation shaft for freely rotating the body to be rotated back and forth. The rotation drive unit is arranged in the capsule body in such a way that a first line obtained by linking the positions of center of gravity of cross-sections formed up to a limit of the formation when the capsule body is cut along a plane perpendicular to the rotation shaft does not overlap a second line obtained by extending the rotation shaft as the same line.

29 Claims, 7 Drawing Sheets

INTRACOELOMIC MOBILE BODY, AND CAPSULE-TYPE ULTRASONIC ENDOSCOPE

This application claims benefit of Japanese Application Nos. 2003-377487 filed in Japan on Nov. 6, 2003, 2004-291679 filed in Japan on Oct. 4, 2004, and 2004-316929 filed in Japan on Oct. 29, 2004, the contents of which are incorporated by this reference.

BACKGROUND OF THE INVENTION

1. Field of the Invention

The present invention relates to an intracoelomic mobile body for introduction into a body cavity, and a capsule-type ultrasonic endoscope.

2. Description of the Related Art

In recent years, capsule-type medical apparatuses came into use as intracoelomic mobile bodies for introduction into body cavities.

Such capsule-type medical apparatuses do not require long and thin insertion portions typical for the endoscopes and are so formed as to be easily swallowed by a patient.

For example, a capsule-type ultrasonic endoscope described in Japanese Patent Application Laid-open No. H9-135832 has been proposed as such a conventional capsule-type medical apparatus.

In the capsule-type ultrasonic endoscope described in Japanese Patent Application Laid-open No. H9-135832, ultrasonic tomographic images (referred to hereinbelow as ultrasonic images) are obtained based on echo information obtained by transmitting ultrasonic pulses to a living body tissue and receiving them therefrom. Therefore, with the above-described conventional capsule-type ultrasonic endoscope, ultrasonic images could be acquired by passing the capsule-type ultrasonic endoscope through zones where a long thin insertion portion of the usual ultrasonic endoscope was difficult to insert.

In the conventional capsule-type ultrasonic endoscope, an ultrasonic transducer unit, which is a unit to be rotated, and a drive unit for rotating the ultrasonic transducer unit freely back and forth are enclosed in a capsule sheath serving as a casing. The configuration of the conventional capsule-type ultrasonic endoscope is such that the ultrasonic transducer unit transmits and receives ultrasonic pulses, for example, in the radial direction perpendicular to the longitudinal central axis of the capsule sheath, when the ultrasonic transducer unit is rotated by the drive unit.

SUMMARY OF THE INVENTION

The intracoelomic mobile body in accordance with the present invention comprises: a capsule body which has a body to be rotated and can be introduced into the human body; and a rotation drive unit which has a rotation shaft for freely rotating the body to be rotated back and forth, the rotation drive unit being arranged in the capsule body in such a way that a first line obtained by linking the positions of center of gravity of cross-sections formed up to a limit of the formation when the capsule body is cut along a plane perpendicular to the rotation shaft does not overlap a second line obtained by extending the rotation shaft as the same line.

Further, the capsule-type medical apparatus in accordance with the present invention comprises: a capsule body which has a body to be rotated and can be introduced into the human body; and a rotation drive unit which has a rotation shaft for freely rotating the body to be rotated back and forth, the rotation drive unit being arranged in the capsule body in such a way that a first line obtained by linking the positions of center of gravity of cross-sections formed up to a limit of the formation when the capsule body is cut along a plane perpendicular to the rotation shaft does not overlap a second line obtained by extending the rotation shaft as the same line.

Furthermore, the capsule-type ultrasonic endoscope in accordance with the present invention comprises: an ultrasonic transducer which can generate ultrasonic waves; a capsule body which has the ultrasonic transducer and can be introduced into the human body; and a rotation drive unit which has a rotation shaft for rotating the ultrasonic transducer, the rotation drive unit being arranged in the capsule body in such a way that a first line obtained by linking the positions of center of gravity of cross-sections formed up to a limit of the formation when the capsule body is cut along a plane perpendicular to the rotation shaft does not overlap a second line obtained by extending the rotation shaft as the same line.

DETAILED DESCRIPTION OF THE PREFERRED EMBODIMENTS

The preferred embodiments of the present invention will be described hereinbelow with reference to the appended drawings.

In the preferred embodiments, the present invention is applied to a capsule-type ultrasonic endoscope as an intracoelomic mobile body as one embodiment.

First Embodiment

FIGS. 1 to 5 illustrate a first embodiment of the capsule-type ultrasonic endoscope in accordance with the present invention.

Figure 1:
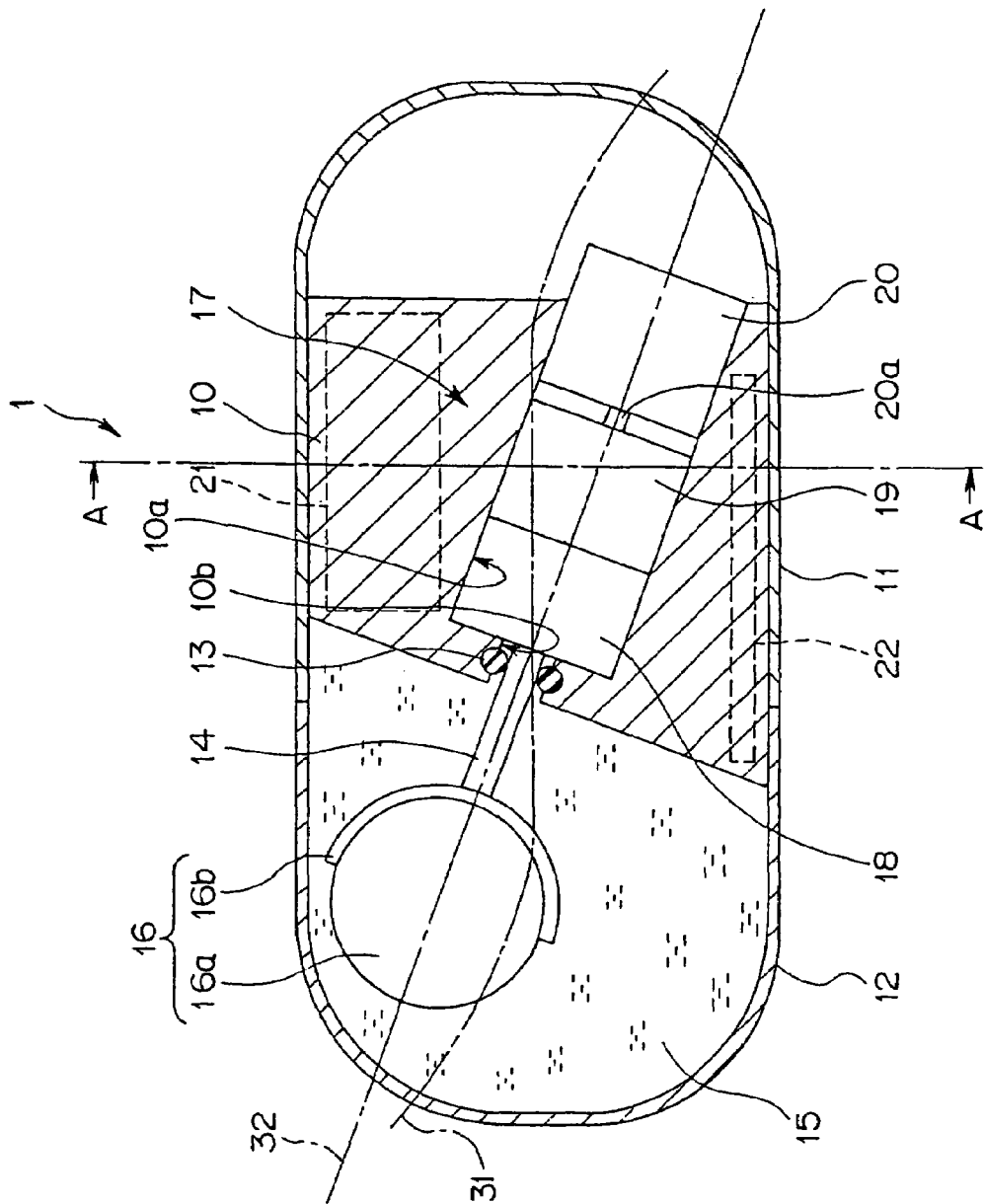
FIG. 1 is a structural diagram of the capsule-type ultrasonic endoscope of a first embodiment.

As shown in FIG. 1, in a capsule-type ultrasonic endoscope 1 of the first embodiment as an intracoelomic mobile body, a body cover 11 with the end portions formed to have a semi-spherical shape and a transducer cover 12 are integrated as a capsule sheath with a base part 10 of an almost tubular shape. Thus, with the base part 10 as a basic structure and the body cover 11 and transducer cover 12 as a casing, the capsule-type ultrasonic endoscope 1 is formed as a capsule body.

The body cover 11 is water-tightly and fixedly disposed in one end portion of the base part 10, and the transducer cover 12 is water-tightly and fixedly disposed in the other end portion. A central through hole comprising a central large-diameter hole 10a and a central small-diameter hole 10b is formed in the central portion of the base part 10.

An O-ring 13 is disposed in the central small-diameter hole 10b. This O-ring 13 is in intimate contact with the outer peripheral surface of a transducer shaft 14 and the inner peripheral surface of the central small-diameter hole 10b, thereby ensuring hermeticity and also supporting the transducer shaft 14. An ultrasonic transfer medium 15 such as fluid paraffin, water, and aqueous solution of carboxymethyl cellulose is sealed in the inner space formed by the transducer cover 12, base part 10, and O-ring 13.

On the other hand, a rotation drive unit 17 is provided in the central large-diameter hole 10a. The rotation drive unit 17 serves to rotate an ultrasonic transducer unit 16 as a body to be rotated serving as an information acquisition unit for acquiring biological information. An image pickup unit or the like (not shown in the figure) which is rotated by the rotation drive unit 17 may be also provided as the information acquisition unit.

The rotation drive unit 17 comprises a slip ring 18, an encoder 19, and a drive motor 20. The transducer shaft 14 is rotatably supported, for example, by a ball bearing provided in the slip ring 18. A rotation shaft 20a which is the drive shaft of the drive motor 20 and the transducer shaft 14 are mechanically integrated.

The ultrasonic transducer unit 16 is provided in the distal end portion of the transducer shaft 14. The ultrasonic transducer unit 16 comprises an ultrasonic transducer 16a and a transducer holding member 16b for holding the ultrasonic transducer 16a.

A power source unit 21 and a circuit substrate 22 are also provided in the base part 10.

A drive motor rotation control circuit, a transmitting and receiving circuit, a signal processing circuit, and a wireless transmission circuit (not shown in the figure) are provided at the circuit substrate 22.

The drive motor rotation control circuit is designed to conduct rotation control of the drive motor 20 with electric power supplied from the power source unit 21. The transmitting and receiving circuit is designed to conduct transmission of ultrasonic pulses to the ultrasonic transducer 16a and reception of pulses therefrom via the slip ring 18. The signal processing circuit is designed to process the signals received from the transmitting and receiving circuit. The wireless transmission circuit serves to conduct the prescribed signal processing of echo signals processed with the signal processing circuit and wireless transmit them to the ultrasonic observation apparatus.

An input/output cable (not shown in the figure) of the ultrasonic transducer 16a is electrically connected to a ring portion (not shown in the figure) of the slip ring 18 which is rotation-type signal transmission means and, via a metal brush, to a cable on the output side of the slip ring 18.

Here, in the present embodiment, the rotation drive unit 17 is arranged such that a capsule center of gravity line 31 (first line) obtained by linking the positions of center of gravity of cross-sections formed up to a limit of the formation of the capsule-type endoscope 1, i.e. within the casing (body cover 11 and transducer cover 12) when the capsule-type ultrasonic endoscope 1 is cut along a plane perpendicular to the rotation shaft 20a of the rotation drive unit 17 (drive motor 20) calculated in case a constant mass distribution is assumed, does not overlap the center line 32 (second line) of the rotation drive unit 17, i.e. the axis line obtained by extending the rotation shaft 20a of the rotation drive unit 17 as the same line.

More specifically, the capsule-type ultrasonic endoscope 1 is disposed such that the rotation shaft 20a of the rotation drive unit 17, i.e. the center axis 32 is inclined by a predetermined angle with respect to the capsule center of gravity line 31 by arranging the rotation drive unit 17 inclined with respect to the capsule center of gravity line 31.

Figure 2:
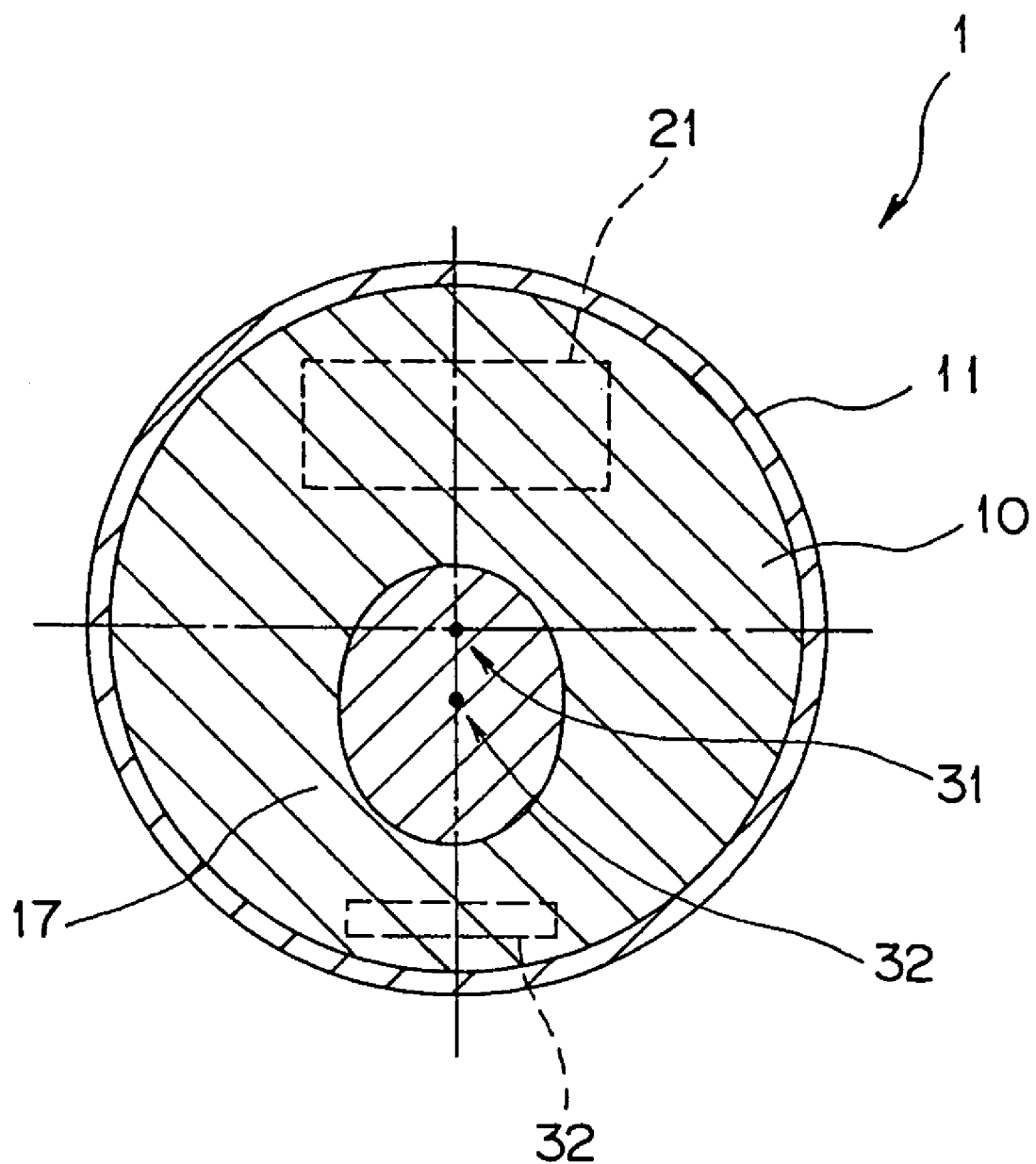
FIG. 2 is an A-A cross-sectional view of the capsule-type ultrasonic endoscope shown in FIG. 1.

As a result, in the capsule-type ultrasonic endoscope 1 shown in FIG. 2, the capsule center of gravity line 31 and the central axis 32 of the rotation drive unit 17 do not overlap, at least partially. As shown in FIG. 1, the capsule center of gravity line 31 forms a curved line which is bent toward the ultrasonic transducer 16 in the distal end side thereof and toward the rotation drive unit 17 in the rear end side thereof. The distance between the capsule center of gravity line 31 and the central axis 32 of the rotation drive unit 17 is less than about 10 mm.

Here, the equation of motion of a rigid body having a fixed axis is generally as follows:

$$I\alpha = N$$

where
I: inertia moment,
$\alpha$: angular acceleration,
N: moment of external force.

Therefore, if we consider a case where a certain constant moment is applied, the larger the inertia moment of the rigid body is, the harder it is for the rigid body to move.

On the other hand, if the inertia moment around an axis passing through the center of gravity is denoted by $I_G$, then the inertia moment around the parallel axis at a distance of h from the center of gravity will be as follows:

$$I = I_G + Mh^2$$

where M: mass of the rigid body.

Therefore, if the center of rotation is located in the position at a distance from the center of gravity, then the inertia moment further increases. Thus, it is hard for the rigid body to rotate.

In the above-described case, the rigid body was in vacuum, but actually a fluid is present. Therefore, fluid resistance acting on the body surface has to be taken into account.

When the cross section is round, only a friction drag acts between a body surface and a fluid when the body rotates about the axis passing through the center of gravity. On the other hand, when the body rotates about an axis located at a distance from the center of gravity, the rotations are similar to rotations in a wooden pestle. Therefore, a pressure drag acts in addition to the aforementioned friction drag.

The pressure drag is generally larger than the friction drag. Furthermore, because the pressure drag increases with the distance of the rotation center from the center of gravity, the rotation load on the body increases. This also shows that if the rotation center is located in a position at a distance from the center of gravity, it is hard for the body to rotate.

Figure 3:
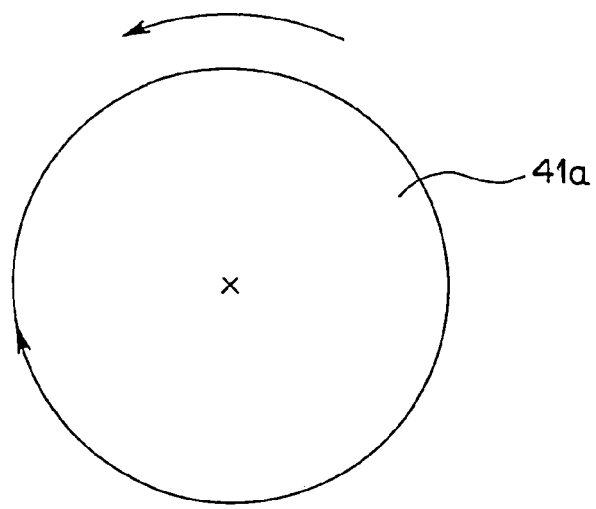
FIG. 3 is a schematic drawing illustrating the case in which the rotation center of a rigid body is in the center of gravity and only friction drag acts.

When the rotation center of the rigid body 41a is in the center of gravity, as shown in FIG. 3, only the friction drag acts and the body rotates easily.

Figure 4:
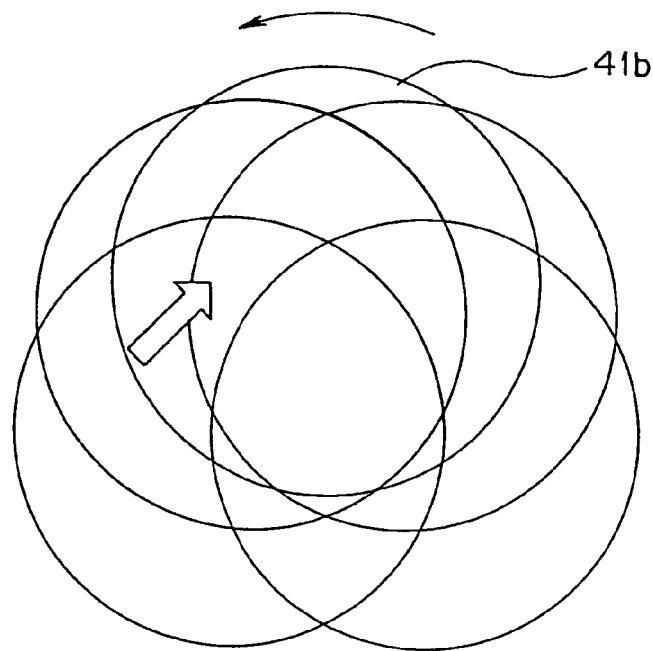
FIG. 4 is a schematic drawing illustrating the case in which the rotation center of a rigid body is not in the center of gravity and pressure drag acts.

On the other hand, when the rotation center of the rigid body 41b is not in the center of gravity, as shown in FIG. 4, the pressure drag acts and the body is hard to rotate.

Therefore, when the rotation drive unit 17 drives and the ultrasonic transducer unit 16 rotates, producing a moment, the larger is the distance between this rotation shaft, that is, the central axis 32 of the rotation drive unit 17, and the axis passing through the center of gravity of the capsule contour, that is, the capsule center of gravity line 31, the harder it is for the capsule-type ultrasonic endoscope 1 to rotate.

Therefore, when the rotation drive unit 17 is driven and the ultrasonic transducer unit 16 rotates, no inertia force is generated with respect to the capsule center of gravity line 31 and the capsule-type ultrasonic endoscope 1 can be prevented from rotating.

In the present embodiment, as described hereinabove, the rotation shaft 20a of the rotation drive unit 17 is inclined at the prescribed angle in the direction tilted with respect to the longitudinal central axis of the casing (body cover 11 and transducer cover 12). As a result, in the capsule-type ultrasonic endoscope 1, the ultrasonic transducer 16a transmits and receives ultrasonic pulses from the radial direction inclined at the prescribed angle from the vertical direction with respect to the longitudinal central axis of the casing and an ultrasonic image is obtained from the direction inclined at the prescribed angle from the vertical direction with respect to the longitudinal central axis of the casing.

The capsule-type ultrasonic endoscope 1 is swallowed by a patient and ultrasonic observations are conducted.

If the power source unit 21 in the capsule-type ultrasonic endoscope 1 is set in a power supply mode, a drive signal is outputted from the drive motor rotation control circuit located on the circuit substrate 22 and the rotation shaft 20a of the rotation drive unit 17 starts rotating. As a result, in the capsule-type ultrasonic endoscope 1, the transducer shaft 14 rotates and the ultrasonic transducer unit 16 starts rotating.

In the capsule-type ultrasonic endoscope 1, as described hereinabove, the rotation shaft 20a of the rotation drive unit 17 is positioned with inclination at the prescribed angle in the direction tilted with respect to the longitudinal central axis of the casing (body cover 11 and transducer cover 12). Therefore, the capsule center of gravity line 31 and central axis 32 of the rotation drive unit 17 assume different positions, that is, do not overlap, at least partially.

Therefore, when the rotation drive unit 17 is driven and the ultrasonic transducer unit 16 rotates, as described hereinabove, the action of the friction drag hardly causes rotation, no inertia force is generated with respect to the capsule center of gravity line 31, and no rotation proceeds.

Further, a transducer drive signal is outputted to the ultrasonic transducer 16a from the transmitting and receiving circuit located on the circuit substrate 22. This transducer drive signal is supplied to the ultrasonic transducer 16a via the slip ring 18 or the like. As a result, the ultrasonic transducer 16a transmits ultrasonic pulses to a living body tissue and receives them therefrom, conducts radial scanning, and obtains echo signals from the living body tissue.

The echo signals obtained from the ultrasonic transducer 16a are transmitted to the transmitting and receiving circuit via the slip ring 18 and transmitted to the signal processing circuit. The signal processing circuit generates ultrasonic signals from the received echo signals and sends the ultrasonic signals to the ultrasonic observation apparatus via a wireless transmission circuit. The ultrasonic observation apparatus conducts signal processing of the echo signals obtained from the capsule-type ultrasonic endoscope 1, creates ultrasonic image data, and displays the ultrasonic image data on a monitor (not shown in the figure).

As a result, the capsule-type ultrasonic endoscope 1 of the first embodiment is not only small and easy to swallow, but it also makes it possible to prevent the rotation of the base part 10 even if the rotation drive unit 17 is driven and the ultrasonic transducer unit 16 rotates.

Although the capsule center of gravity line 31 (first line) and the central line 32 (second line) are drawn in the two-dimensional relation, it is possible as a matter of course that the capsule center of gravity line 31 (first line) and the central line 32 (second line) are in the three-dimensional relation. It is also possible as a matter of course that the capsule center of gravity line 31 (first line) and the central line 32 (second line) are in a twisted relation. On such occasion, it makes it possible to further prevent the capsule-type ultrasonic endoscope 1 from rotating by the rotation of the rotation drive unit 17.

Further, in the capsule-type ultrasonic endoscope 1, as described hereinabove, the rotation shaft 20a of the rotation drive unit 17 is inclined at the prescribed angle in the direction tilted with respect to the longitudinal central axis of the casing (body cover 11 and transducer cover 12). Therefore, the ultrasonic image obtained is also inclined at the prescribed angle from the vertical direction with respect to the longitudinal central axis.

Figure 5:
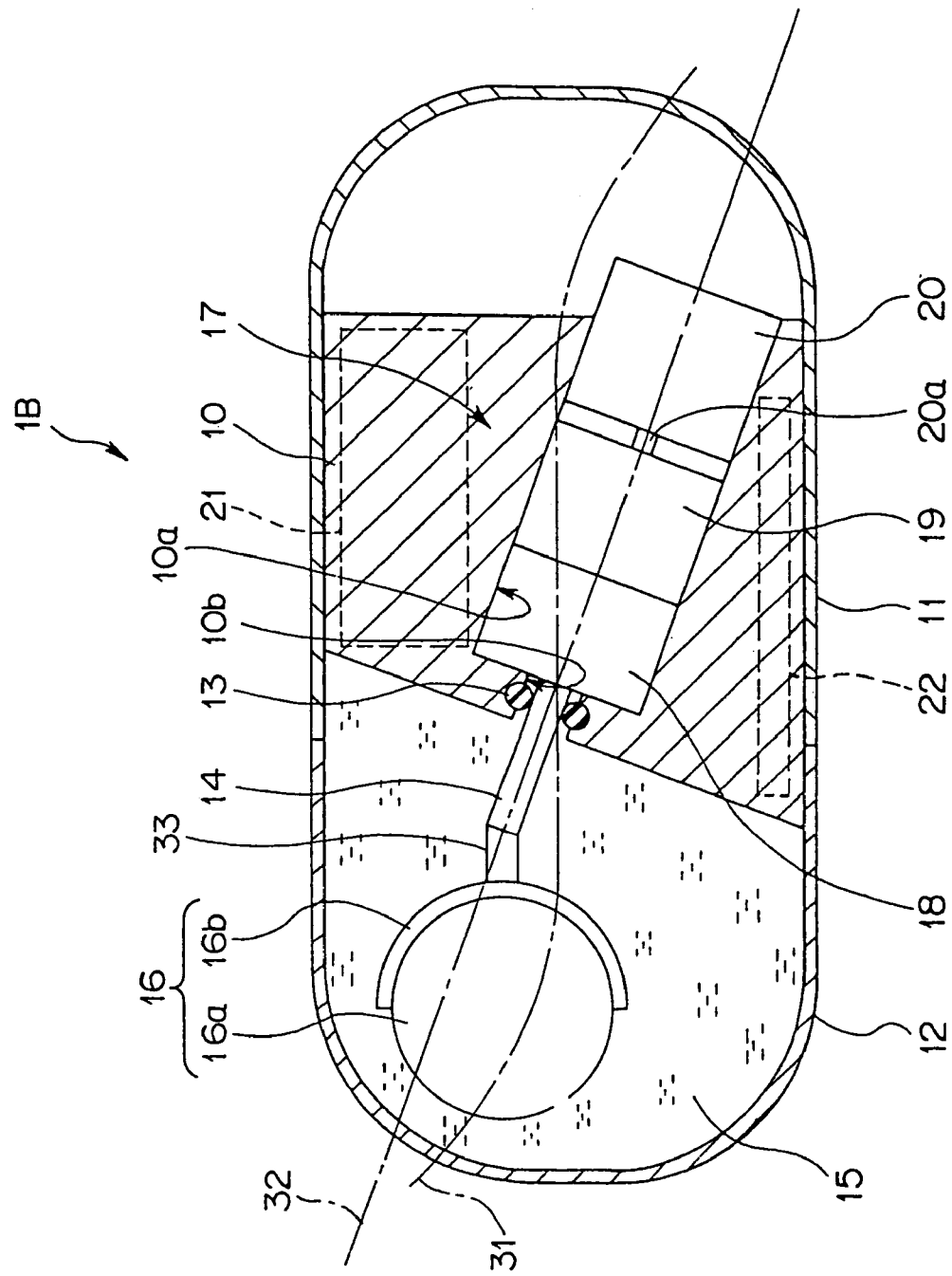
FIG. 5 is a structural diagram illustrating the modification example of the capsule-type ultrasonic endoscope shown in FIG. 1.

Here, as shown in FIG. 5, a configuration may be used in which a flexible coupling is used to obtain an ultrasonic image in the direction perpendicular to the longitudinal central axis of the casing (body cover 11 and transducer cover 12).

As shown in FIG. 5, the capsule-type ultrasonic endoscope 1B has a configuration in which a flexible coupling 33 is connected to the transducer shaft 14 and the ultrasonic transducer unit 16 becomes parallel to the longitudinal central axis of the casing (body cover 11 and transducer cover 12).

As a result, in the capsule-type ultrasonic endoscope 1B, the ultrasonic transducer 16a can transmit and receive ultrasonic pulses in the radial direction, which is a direction perpendicular to the longitudinal central axis of the casing (body cover 11 and transducer cover 12), and obtain ultrasonic images in the direction perpendicular to the longitudinal central axis. The flexible coupling shown in FIG. 5 may be a gear, a flexible shaft, or the like.

Second Embodiment

Figure 6:
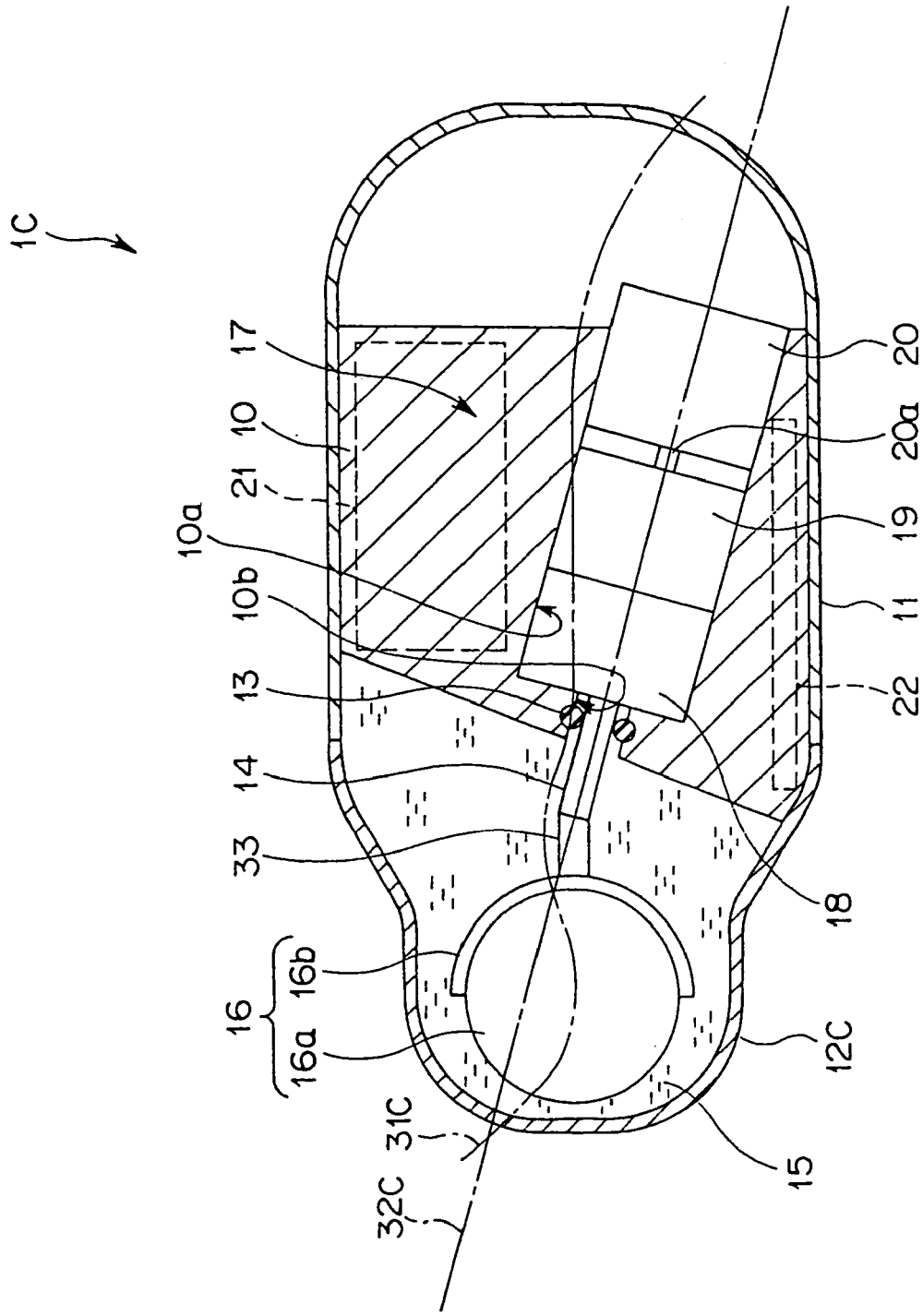
FIG. 6 is a structural diagram of the capsule-type ultrasonic endoscope of a second embodiment.

FIG. 6 shows a second embodiment of the capsule-type ultrasonic endoscope in accordance with the present invention.

In the above-described first embodiment, the rotation shaft 20a of the rotation drive unit 17 was set in a position inclined at the prescribed angle with respect to the longitudinal central axis of the casing by disposing the rotation drive unit 17 with inclination with respect to the longitudinal central axis of the casing (body cover 11 and transducer cover 12). However, in the lower half-circle portion in the radial scanning plane where the distance from the ultrasonic transducer unit 16 to the transducer cover 12 is large, the attenuation quantity of ultrasonic pulses emitted from the transducer cover 12 becomes large. Accordingly, in the second embodiment, a configuration is employed in which the distance from the rotation center of the ultrasonic transducer 16a to the transducer cover 12 is constant (equidistant configuration) in the radial scanning plane. Other configurations are identical to those of the first embodiment and the explanation thereof is omitted. In the explanation below, identical structural components are assigned with the same reference symbols.

Thus, as shown in FIG. 6, in the capsule-type ultrasonic endoscope 1C of the second embodiment, the transducer cover 12C is formed to have a tumbler-like shape so that the distance from the rotation center of the ultrasonic transducer 16a in the radial scanning plane can be the same (equidistant configuration).

In the capsule-type ultrasonic endoscope 1C, similarly to the configuration explained in the first embodiment, the rotation shaft 20a of the rotation drive unit 17 is positioned with inclination at the prescribed angle in the tilted direction with respect to the longitudinal central axis of the casing (body cover 11 and transducer cover 12C). Therefore, the configuration of the capsule-type ultrasonic endoscope 1C is such that the capsule center of gravity line 31C and the central axis 32 of the rotation drive unit 17 assume different positions, that is, do not overlap, at least partially.

Because the ultrasonic transducer 16 is disposed on the lower side, the capsule center of gravity line 31C forms a curved line which rapidly decreases and then somewhat rises on the distal end side, as compared with the capsule center of gravity line 31.

Therefore, with the capsule-type ultrasonic endoscope 1C, when the rotation drive unit 17 is driven and the ultrasonic transducer unit 16 rotates, the rotation of the endoscope is made difficult by the action of the friction drag, as described hereinabove, no inertia force is generated with respect to the capsule center of gravity line 31C and the endoscope is not rotated.

Further, in the capsule-type ultrasonic endoscope 1C, a flexible coupling 33 is connected to the transducer shaft 14 and the ultrasonic transducer unit 16 becomes parallel to the longitudinal central axis of the casing (body cover 11 and transducer cover 12C). Other configurations are identical to those of the first embodiment and the explanation thereof is omitted.

The capsule-type ultrasonic endoscope 1C is swallowed by a patient and ultrasonic observations are conducted in the same manner as was explained in the first embodiment.

If the power source unit 21 in the capsule-type ultrasonic endoscope 1C is set in a power supply mode, a drive signal is outputted from the drive motor rotation control circuit located on the circuit substrate 22 and the rotation shaft 20a of the rotation drive unit 17 starts rotating. As a result, in the capsule-type ultrasonic endoscope 1C, the transducer shaft 14 rotates and the ultrasonic transducer unit 16 starts rotating.

Further, a transducer drive signal is outputted to the ultrasonic transducer 16a from the transmitting and receiving circuit located on the circuit substrate 22. This transducer drive signal is supplied to the ultrasonic transducer 16a via the slip ring 18 or the like. As a result, the ultrasonic transducer 16a transmits ultrasonic pulses to a living body tissue and receives them therefrom, conducts radial scanning, and obtains echo signals from the living body tissue.

In the capsule-type ultrasonic endoscope 1C, as described hereinabove, the transducer cover 12C is formed so that the distance from the rotation center of the ultrasonic transducer 16a is constant (equidistant configuration) in the radial scanning plane. Therefore, in the capsule-type ultrasonic endoscope 1C, the attenuation quantity of ultrasonic pulses produced by the ultrasonic transducer 16a is constant regardless of the orientation of the ultrasonic transducer 16a.

The echo signals obtained from the ultrasonic transducer 16a are transmitted to the transmitting and receiving circuit via the slip ring 18 and transmitted to the signal processing circuit. The signal processing circuit generates ultrasonic signals from the received echo signals and sends the ultrasonic signals to the ultrasonic observation apparatus via a wireless transmission circuit. The ultrasonic observation apparatus conducts signal processing of the echo signals obtained from the capsule-type ultrasonic endoscope 1C, creates ultrasonic image data, and displays the ultrasonic-image data on a monitor (not shown in the figure).

Therefore, in the capsule-type ultrasonic endoscope 1C, the attenuation quantity of ultrasonic pulses in the radial scanning plane is constant, regardless of the orientation of the ultrasonic transducer 16a, and echo signals from the living body tissue can be obtained.

As a result, with the capsule-type ultrasonic endoscope 1C, in addition to obtaining the same effect as in the first embodiment, the attenuation quantity of ultrasonic pulses produced by the ultrasonic transducer 16a is constant, regardless of the orientation of the ultrasonic transducer 16a, and good ultrasonic image can be obtained.

Third Embodiment

Figure 7:
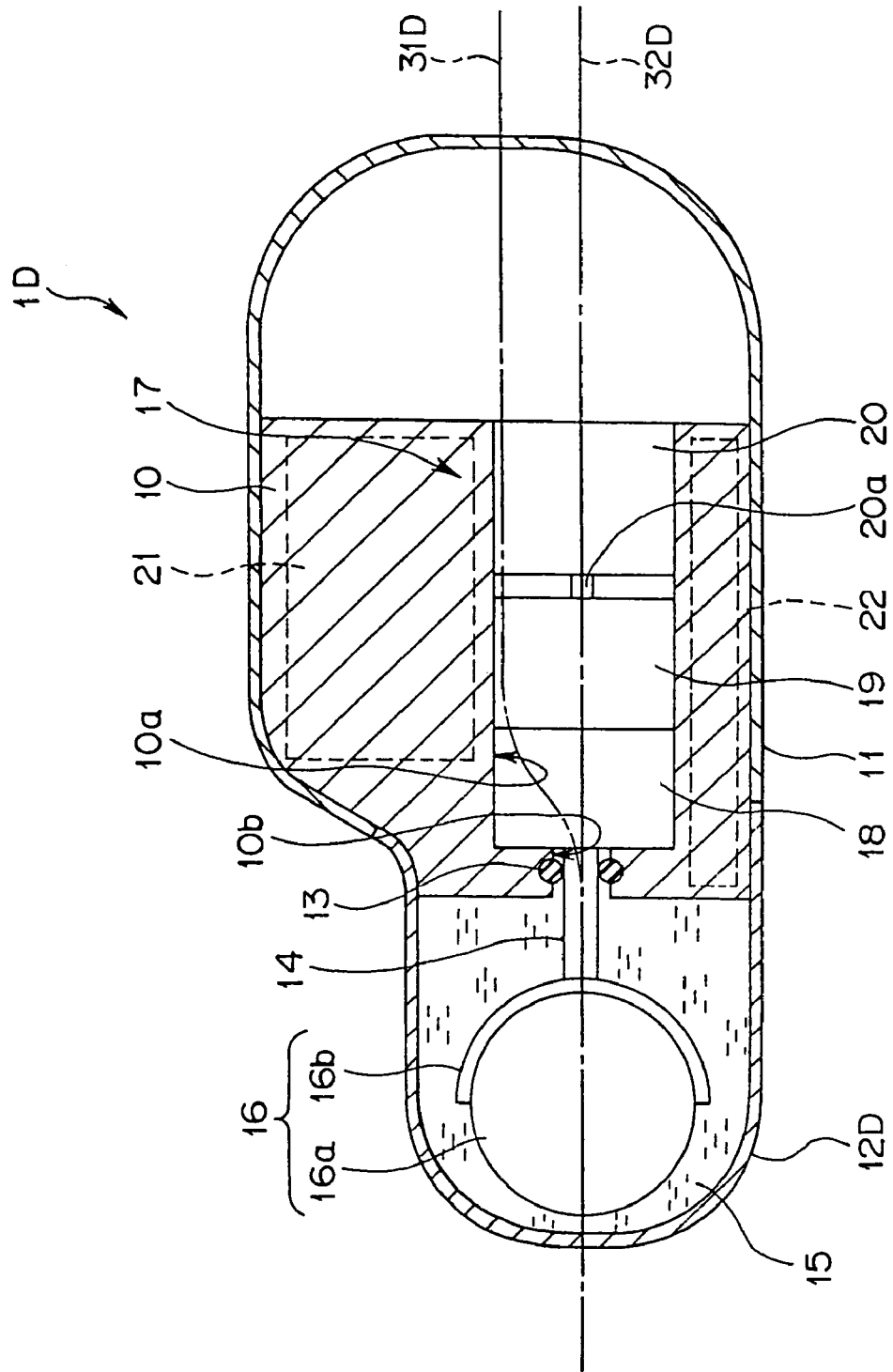
FIG. 7 is a structural diagram of the capsule-type ultrasonic endoscope of a third embodiment.
Figure 8:
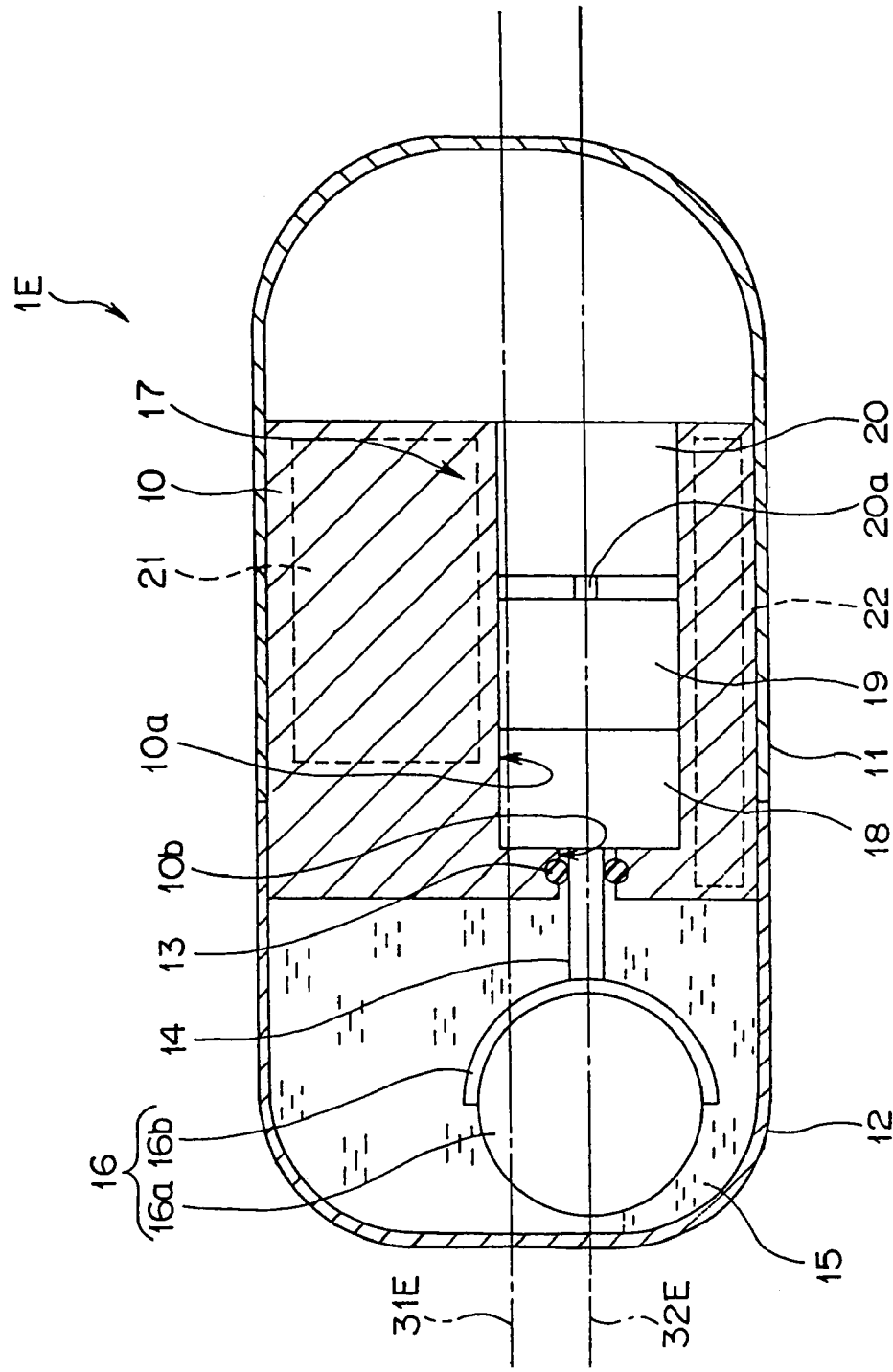
FIG. 8 is a structural diagram illustrating the modification example of the capsule-type ultrasonic endoscope shown in FIG. 7.

FIG. 7 and FIG. 8 illustrate a third embodiment of the capsule-type ultrasonic endoscope in accordance with the present invention.

The configuration of the above-described first and second embodiments was such that the rotation shaft 20a of the rotation drive unit 17 was in a position inclined at the prescribed angle in the direction tilted with respect to the longitudinal central axis of the casing. By contrast, the configuration of the third embodiment is such that the rotation drive unit 17 is disposed eccentrically with respect to the longitudinal central axis of the casing. As a result, the rotation shaft 20a of the rotation drive unit 17 assumes a position which is eccentric with respect to the longitudinal central axis of the casing. Other configurations are identical to those of the first embodiment and the explanation thereof is therefore omitted. The explanation hereinbelow will be conducted by assigning the same components with the same reference symbols.

Thus, as shown in FIG. 7, the configuration of the capsule-type ultrasonic endoscope 1D of the third embodiment is such that the rotation shaft 20a of the rotation drive unit 17 assumes a position which is eccentric with respect to the longitudinal central axis of the casing (body cover 11 and transducer cover 12D).

More specifically, in the capsule-type ultrasonic endoscope 1D, because the rotation drive unit 17 is disposed eccentrically with respect to the longitudinal central axis of the casing (body cover 11 and transducer cover 12D), the rotation shaft 20a of the rotation drive unit 17 is eccentric with respect to the longitudinal central axis of the casing (body cover 11 and transducer cover 12D).

For this reason, in the capsule-type ultrasonic endoscope 1D, because the rotation shaft 20a of the rotation drive unit 17 is eccentric with respect to the longitudinal central axis of the casing (body cover 11 and transducer cover 12D), the capsule center of gravity line 31D and the central axis 32D of the rotation drive unit 17 assume different positions, that is, do not overlap, at least partially.

Further, because the rotation drive unit 17 is disposed, parallel to the longitudinal central axis of the casing (body cover 11 and transducer cover 12D) and also the rotation shaft 20a thereof is disposed parallel to the longitudinal central axis of the casing (body cover 11 and transducer cover 12D) and the transducer cover 12D is formed to have an almost R-like shape, the capsule center of gravity line 31D is formed so that straight lines formed on the distal end side and rear end side are connected by a curved line.

Therefore, with the capsule-type ultrasonic endoscope 1D, when the rotation drive unit 17 is driven and the ultrasonic transducer unit 16 rotates, as described hereinabove, the action of the friction drag hardly causes rotation, no inertia force is generated with respect to the capsule center of gravity line 31D, and no rotation proceeds.

Further, in the capsule-type ultrasonic endoscope 1D, because the ultrasonic transducer unit 16 is parallel to the longitudinal central axis of the base part 10, ultrasonic pulses can be transmitted and received in the radial direction which is a direction perpendicular to the longitudinal central axis of the base part 10.

Further, in the capsule-type ultrasonic endoscope 1D, the transducer cover 12D is formed to have an almost R-like shape so that the distance from the rotation center of the ultrasonic transducer 16a in the radial scanning plane becomes constant (equidistant configuration). Other features are identical to those of the first embodiment and the explanation thereof is omitted.

The capsule-type ultrasonic endoscope 1D is swallowed by a patient and ultrasonic observations are conducted in the same manner as was explained in the first embodiment.

If the power source unit 21 in the capsule-type ultrasonic endoscope 1D is set in a power supply state, a drive signal is outputted from the drive motor rotation control circuit located on the circuit substrate 22 and the rotation shaft 20a of the rotation drive unit 17 starts rotating. As a result, in the capsule-type ultrasonic endoscope 1D, the transducer shaft 14 rotates and the ultrasonic transducer unit 16 starts rotating.

Here, in the capsule-type ultrasonic endoscope 1D, as mentioned above, because the rotation shaft 20a of the rotation drive unit 17 is eccentric with respect to the longitudinal central axis of the casing (body cover 11 and transducer cover 12D), the capsule center of gravity line 31D and the central axis 32D of the rotation drive unit 17 assume different positions, that is, do not overlap, at least partially.

Therefore, with the capsule-type ultrasonic endoscope 1D, when the rotation drive unit 17 is driven and the ultrasonic transducer unit 16 rotates, as described hereinabove, the action of the friction drag hardly causes rotation, no inertia force is generated with respect to the capsule center of gravity line 31D, and no rotation proceeds.

Further, a transducer drive signal is outputted to the ultrasonic transducer 16a from the transmitting and receiving circuit located on the circuit substrate 22. This transducer drive signal is supplied to the ultrasonic transducer 16a via the slip ring 18 or the like. As a result, the ultrasonic transducer 16a transmits the ultrasonic pulses to a living body tissue and receives them therefrom, conducts radial scanning, and obtains echo signals from the living body tissue.

Further, as described hereinabove, in the capsule-type ultrasonic endoscope 1D, the ultrasonic transducer unit 16 is parallel to the longitudinal central axis of the base part 10. Therefore, in the capsule-type ultrasonic endoscope 1D, the ultrasonic transducer 16a can transmit and receive ultrasonic pulses in the radial direction which is the direction perpendicular to the longitudinal central axis of the casing (body cover 11 and transducer cover 12D).

Further, as described hereinabove, in the capsule-type ultrasonic endoscope 1D, the transducer cover 12D is formed so that the distance from the rotation center of the ultrasonic transducer 16a in the radial scanning plane becomes constant (equidistant configuration). Therefore, in the capsule-type ultrasonic endoscope 1D, the attenuation quantity of ultrasonic pulses produced by the ultrasonic transducer 16a is constant regardless of the orientation of the ultrasonic transducer 16a.

Therefore, in the capsule-type ultrasonic endoscope 1D, as described hereinabove, the attenuation quantity of ultrasonic pulses produced by the ultrasonic transducer 16a in the radial scanning plane is constant, regardless of the orientation of the ultrasonic transducer 16a, and echo signals from the living body tissue can be obtained.

The echo signals obtained from the ultrasonic transducer 16a are transmitted to the transmitting and receiving circuit via the slip ring 18 and transmitted to the signal processing circuit. The signal processing circuit generates ultrasonic signals from the received echo signals and sends the ultrasonic signals to the ultrasonic observation apparatus via a wireless transmission circuit. The ultrasonic observation apparatus conducts signal processing of the echo signals obtained from the capsule-type ultrasonic endoscope 1D, creates ultrasonic image data, and displays the ultrasonic image data on a monitor (not shown in the figure).

As a result, with the capsule-type ultrasonic endoscope 1D, in addition to obtaining the same effect as in the second embodiment, the ultrasonic transducer 16a transmits and receives ultrasonic pulses in the radial direction which is a direction perpendicular to the longitudinal central axis of the casing (body cover 11 and transducer cover 12D) and an ultrasonic image with orientation perpendicular to the longitudinal central axis can be obtained despite the fact that the flexible coupling 33 is not used.

Further, in the capsule-type ultrasonic endoscope 1D, the drive motor 20 is disposed eccentrically and parallel to the longitudinal axis direction, without inclination. Therefore, the inner space of the base part 10 can be used more effectively than in the first and second embodiment. Another advantage is that the circuit substrate 22 and power source unit 21 can be easily disposed (laid out).

The capsule center of gravity line 31D is formed so that straight lines formed on the distal end side and rear end side are connected by a curved line.

Here, as shown in FIG. 8, the capsule center of gravity line may be formed as a straight light parallel to the central axis of the rotation drive unit 17.

As shown in FIG. 8, the capsule-type ultrasonic endoscope 1E is formed to have an almost cylindrical casing shape similar to that of the first embodiment. As a result, because the upper side of the transducer cover 12 in the capsule-type ultrasonic endoscope 1E is filled with an ultrasonic transfer medium 15, the capsule center of gravity line 31E is formed as a straight line parallel to the central shaft 32E of the rotation drive unit 17.

Therefore, in the capsule-type ultrasonic endoscope 1E of the present modification example, the drive motor 20 is disposed eccentrically and parallel to the longitudinal axis direction, without inclination, in the same manner as in the capsule-type ultrasonic endoscope 1D. As a result, the inner space of the base part 10 can be used more effectively than in the first and second embodiment and the circuit substrate 22 and power source unit 21 can be easily disposed (laid out). Yet another advantage is that the endoscope has the same diameter from the distal end to the rear end thereof, rather than having an almost R-like shape as in the transducer cover 12D, and can therefore be easily processed.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An intracoelomic mobile body comprising:
 a swallowable capsule body which has an internal body to be rotated, the swallowable capsule body can be introduced into the human body and having first and second ends offset in a longitudinal direction; and
 a rotation drive unit which has a rotation shaft for freely rotating the internal body to be rotated back and forth, the rotation drive unit being arranged in the swallowable capsule body between the first and second ends of the swallowable capsule body in such a way that a first line obtained by linking the positions of center of gravity of cross-sections formed up to limit of the formation when the capsule body is cut along a plane perpendicular to the rotation shaft does not overlap a second line obtained by extending the rotation shaft as the same line.

2. The intracoelomic mobile body according to claim 1, wherein the internal body to be rotated is an information acquisition unit for acquiring biological information.

3. The intracoelomic mobile body according to claim 2, wherein the information acquisition unit is an ultrasonic transducer unit for transmitting and receiving ultrasonic waves.

4. The intracoelomic mobile body according to claim 3, wherein the first line and the second line do not overlap at all.

5. The intracoelomic mobile body according to claim 2, wherein the information acquisition unit is an image pickup unit for picking up optical images.

6. The intracoelomic mobile body according to claim 3, wherein the first line is a straight line.

7. The intracoelomic mobile body according to claim 6, wherein the first line and the second line are not parallel.

8. The intracoelomic mobile body according to claim 6, wherein the first line and the second line are substantially parallel.

9. The intracoelomic mobile body according to claim 8, wherein the distance between the first line and the second line is less than about 10 mm.

10. The intracoelomic mobile body according to claim 3, wherein the first line is formed from a combination of a straight line and a curved line.

11. The intracoelomic mobile body according to claim 10, wherein the first line has at least two straight lines and at least one of the straight lines overlaps the second line.

12. The intracoelomic mobile body according to claim 3, wherein the rotation drive unit is arranged in the capsule body in such a way that the first line and the second line form an angle.

13. The intracoelomic mobile body according to claim 3, wherein the rotation drive unit is arranged in the capsule body in such a way that the second line is eccentric from the first line.

14. A capsule-type ultrasonic endoscope comprising:
a swallowable capsule body which has an internal body to be rotated, the swallowable capsule body can be introduced into the human body and having first and second ends offset in a longitudinal direction; and
a rotation drive unit which has a rotation shaft for freely rotating the internal body to be rotated back and forth, the rotation drive unit being arranged in the swallowable capsule body between the first and second ends of the swallowable capsule body in such a way that a first line obtained by linking the positions of center of gravity of cross-sections formed up to a limit of the formation when the capsule body is cut along a plane perpendicular to the rotation shaft does not overlap a second line obtained by extending the rotation shaft as the same line.

15. The capsule-type ultrasonic endoscope according to claim 14, wherein the internal body to be rotated is an information acquisition unit for acquiring biological information.

16. The capsule-type ultrasonic endoscope according to claim 15, wherein the information acquisition unit is an ultrasonic transducer unit for transmitting and receiving ultrasonic waves.

17. The capsule-type ultrasonic endoscope according to claim 16, wherein the first line and the second line do not overlap at all.

18. The capsule-type ultrasonic endoscope according to claim 15, wherein the information acquisition unit is an image pickup unit for picking up optical images.

19. The capsule-type ultrasonic endoscope according to claim 16, wherein the first line is a straight line.

20. The capsule-type ultrasonic endoscope according to claim 19, wherein the first line and the second line are not parallel.

21. The capsule-type ultrasonic endoscope according to claim 18, wherein the first line and the second line are substantially parallel.

22. The capsule-type ultrasonic endoscope according to claim 21, wherein the distance between the first line and the second line is less than about 10 mm.

23. The capsule-type ultrasonic endoscope according to claim 16, wherein the first line is formed from a combination of a straight line and a curved line.

24. The capsule-type ultrasonic endoscope according to claim 23, wherein the first line has at least two straight lines and at least one of the straight lines overlaps the second line.

25. The capsule-type ultrasonic endoscope according to claim 16, wherein the rotation drive unit is arranged in the capsule body in such a way that the first line and the second line form an angle.

26. The capsule-type ultrasonic endoscope according to claim 16, wherein the rotation drive unit is arranged in the capsule body in such a way that the second line is eccentric from the first line.

27. A capsule-type ultrasonic endoscope comprising:
a swallowable capsule body which can be introduced into the human body, the swallowable capsule body having first and second ends offset in a longitudinal direction;
an ultrasonic transducer internal to the swallowable capsule body and which can generate ultrasonic waves; and
a rotation drive unit which has a rotation shaft for rotating the ultrasonic transducer, the rotation drive unit being arranged in the swallowable capsule body between the first and second ends of the swallowable capsule body in such a way that a first line obtained by linking the positions of center of gravity of cross-sections formed up to a limit of the formation when the capsule body is cut along a plane perpendicular to the rotation shaft does not overlap a second line obtained by extending the rotation shaft as the same line.

28. The capsule-type ultrasonic endoscope according to claim 27, wherein the rotation drive unit is arranged in the capsule body in such a way that the first line and the second line form an angle.

29. The capsule-type ultrasonic endoscope according to claim 27, wherein the rotation drive unit is arranged in the capsule body in such a way that the second line is eccentric from the first line.

* * * * *